United States Patent [19]
Graessle et al.

[11] Patent Number: 5,334,841
[45] Date of Patent: Aug. 2, 1994

[54] METHOD AND APPARATUS FOR DETECTING FLUORESCENCE

[75] Inventors: Josef A. Graessle, Kaarst; Werner R. Schwarz, Leverkusen, both of Fed. Rep. of Germany; William E. Foltz, Cottage Grove, Minn.

[73] Assignee: Minnesota Mining and Manufacturing Company, St. Paul, Minn.

[21] Appl. No.: 7,758

[22] Filed: Jan. 22, 1993

[51] Int. Cl.5 .............................................. G01N 21/64
[52] U.S. Cl. ................... 250/458.1; 250/459.1; 250/461.1
[58] Field of Search ............ 250/252.1 A, 458.1, 250/461.1, 459.1, 461.2; 356/317

[56] References Cited

U.S. PATENT DOCUMENTS

| | | | |
|---|---|---|---|
| 4,622,468 | 11/1986 | Stefanski et al. | 250/458.1 |
| 4,626,684 | 12/1986 | Landa | 250/328 |
| 4,668,868 | 5/1987 | Noller | 250/458 |
| 5,030,297 | 7/1991 | Vespermann et al. | 148/12 F |
| 5,030,832 | 7/1991 | Williams et al. | 250/458.1 |
| 5,032,730 | 7/1991 | Iwasaki | 250/461.2 |
| 5,063,297 | 11/1991 | Hardenbrook et al. | 250/458.1 |
| 5,073,488 | 12/1991 | Matner et al. | 435/31 |

Primary Examiner—Carolyn E. Fields
Attorney, Agent, or Firm—Gary L. Griswold; Walter N. Kirn; William D. Bauer

[57] ABSTRACT

An apparatus and method for detecting fluorescence of an unknown target material. An energy source arranged to excite both the target material and the reference material at approximately the excitation wavelength. A reference detector and a target detector are optically arranged to be responsive to light emitted from the reference material and the target material, respectively, at approximately the fluorescing wavelength. A reference measurement means generates a reference output in response to the reference detector in order to determine the amount of fluorescence generated by the reference material. A target measurement means generates a target output in response to the target detector means in order to determine the amount of fluorescence generated by the target material. Reference calibration means varies the electrical voltage supplied to the energy source and calibrates the reference output. Target calibration means calibrates the target output in response to a known target material.

8 Claims, 7 Drawing Sheets

METHOD AND APPARATUS FOR DETECTING FLUORESCENCE

TECHNICAL FIELD

The present invention relates generally to apparatus and methods for detecting fluorescence of a luminescent material and, more particularly, to such methods and apparatus used in sterilization monitors.

BACKGROUND OF THE INVENTION

There are many environments where the sterilization of articles is of critical importance. Hospitals and medical offices must sterilize certain equipment before that equipment can be utilized with surgical procedures or in sterile environments. Also food service environments must take care that their utensils and equipment are sterilized in order to prevent subsequent possible infection of later users.

Commonly the equipment, instruments or materials that are to be sterilized may be subjected to the necessary parameters to achieve sterilization including the interrelated parameters of time, temperature, steam, dry heat, chemicals such as ethylene oxide gas or radiation dosage. The sterilization process is designed to kill living organisms which might otherwise contaminate the goods being sterilized. Steam sterilization ranges from 121–132 degrees Centigrade with exposure times of three minutes at 132 degrees Centigrade to 30 minutes at 121 degrees Centigrade. Ethylene oxide sterilization ranges from 30 to 65 degrees Centigrade with exposure times of one hour to four hours. Dry heat sterilization typically is two hours at 180 degrees Centigrade.

Since it is critical in many environments that the sterilization be complete, frequently sterilization monitors are utilized. Typically, a small vial, or other container, is inserted into the sterilization unit in order to check upon the completeness of the sterilization process. The vial typically will contain living organisms that are provided nourishment and an environment for rapid growth after being subjected to the sterilization process.

The vial can then be checked for growth of the organism after a incubation period. The incubation allows any organism surviving the sterilization process to grow to a detectable level. Survival of the organism indicates an inadequate sterilization process.

In order to properly detect living organisms, typically a substrate material is added to the vial for the living organisms to react with causing the substrate to change color.

Typically, the reading or analysis of the color change has been done manually with observation by the human eye. However, in one sterilization monitor process, a potentially luminescent substrate material is added to the vial for the living organisms to react with. After allowing for a suitable reaction period, the vial is subjected to a fluorescent light, typically an ultraviolet wavelength light, which excites the invisible to the naked eye fluorescence to appear as visible light. The appearance of visible light in the vial when subjected to an exciting fluorescent light would indicate inadequate sterilization, due at least in part to a shortened time period required for the growth of the living organisms, more automated fluorescence detectors are to be utilized.

Further to more rapidly determine the completeness of the sterilization process, it is desired that fluorescence from the luminescent substrate in the vial be measured at a very low threshold, approximately 0.1 picowatt.

U.S. Pat. No. 5,073,488, Matner, Foltz and Woodson, Rapid Method For Determining Efficacy Of A Sterilization Cycle And Rapid Read-out Biological Indicator, assigned to the assignee of the present invention, discloses a method of developing the fluorescing indicator used in a fluorescence detection apparatus.

Unfortunately, the ultraviolet light source typically used tends to be very unstable due in part to variances in the gas ionization at one or more of the cathodes located at each end of the ultraviolet light source. Further, localized heat variations and emission fluctuations cause the output of the ultraviolet light source (lamp) to contain many independently varying harmonics of the power line frequency. The overall crest-to-trough ratio fluctuates similarly. The use of DC coupled amplifiers with low pass filtering to remove these fluctuations is unacceptable because the DC drift would be well in excess of the signal level being measured.

Prior art fluorescence detectors sometimes utilize dual channels to attempt to adjust for these fluctuations. However, a further problem exists when dual channels are utilized or when the target measurement is taken at a different time from the reference. Since, the signal being measured is so small, minor variations in components between dual channels, even with costly matched components, and between different times of measurement can result in a complete "swamping" of the signal to be measured. The result can easily be an inaccurate measurement. In order to compensate for the inherent inaccuracies in measurement, the "growth" period must be expanded (or not reduced) in order to ensure that living organisms, if present, will be detected.

U.S. Pat. No. 4,626,684, Landa, discloses an apparatus for rapidly conducting fluorescence measurements. The electronics of the apparatus utilizes dual channels. One channel detects the fluorescence of the sample. The other channel detects the fluorescence of a reference. The "background" reference fluorescence is subtracted from the signal sample in order to account for the background. However, in order for the reference to be effectively canceled, the dual channels must be exactly matched.

U.S. Pat. No. 4,668,868, Noller, discloses a fluorescence detector for performing fluoroimmunoassays of biological specimens. The light energy from the sample is used to excite a photovoltaic cell. Temperature compensation is provided by a second photovoltaic cell from which light excitation is eliminated. A push button calibrator also used to provide a bias voltage from the voltaic cell with zero input signal which is memorized. A significant disadvantage of the system of Noller is the lack of a reference value. Since fluctuations in the intensity of stimulating radiation may greatly affect the amount of visible light output apparently perceived can vary greatly.

U.S. Pat. No. 5,030,832, Williams et al, Apparatus For Detecting Fluorescence Of A Luminescent Material, assigned to the assignee of the present invention discloses the construction and operation of an electronic instrument for go/no-go measurement of a fluorescing sterilization monitor. An electronic circuit follows the power fluctuation of the excitation light source and thus follows the variations of the light output. Calibration of this system is manual.

U.S. Pat. No. 5,063,297, Hardenbrook et al, Apparatus For Detecting Fluorescence Of A Luminescent Material, assigned to the assignee of the present invention, is a continuation-in-part of the Williams '297 patent and discloses a single channel detector circuit.

SUMMARY OF THE INVENTION

The present invention provides an apparatus and method for detecting fluorescence to determine the relative fluorescence of a sterilization monitor vial. The apparatus and method provides for automated calibration to insure initial calibration, stabilization and accuracy within critical limits.

Generally, automated operation of the apparatus and method of the present consists of three phases. Each phase must be successfully executed before the next can begin.

First, when the apparatus is energized and before it is operational, a sequence of steps sets the operating voltage level of the excitation light source and the associated reference signal level.

Second, following this first calibration step, the operator inserts a new and unused vial selected from the current production lot being used for sterilization monitoring. The unused vial has not been subjected to an incubation and accordingly no growth of the organisms has occurred. This vial then only gives a minimal fluorescence which is subject to the calibration in this step. The apparatus then calibrates the vial measurement signal to match the reference signal. At this point the new vial is removed and the unit remains in a standby status until test (target) vials are ready for analysis.

Third, following this second calibration step the apparatus is ready for actual vial monitoring. A test (target) vial is inserted into the apparatus. The excitation lamp is energized to full voltage, after a stabilization period, the vial light emissions are measured, compared with each other for stability, and the lamp voltage is compared with set up. If the vial measurements fall within a stable range and lamp voltage measurement is within specifications, the apparatus compares the average test vial emission with the calibration value. If the measured result is within the calibration value indicating that no active material is present in the test vial, an indicator is set. If the measured result is outside the calibration value plus a predetermined threshold value indicating that active material is still present in the vial a different indicator is set. If the various measurements are not stable, a warning signal is set.

The present invention provides an apparatus for detecting fluorescence of an unknown target material being excitable at an excitation wavelength and fluorescing at a fluorescing wavelength. An energy source is arranged to excite both the target material and a reference material at approximately the excitation wavelength. A power supply supplies electrical power having an adjustable voltage to the energy source. An excitation filter is optically arranged between the energy source and both of the target material and the reference material, the excitation filter passing light energy at approximately the excitation wavelength. A reference detector is optically arranged to be responsive to and for detecting light emitted from the reference material at approximately the fluorescing wavelength. A target detector is optically arranged to be responsive to and for detecting light emitted from the target material at approximately the fluorescing wavelength. Reference measurement means generates a reference output in response to the reference detector means in order to determine the amount of fluorescence generated by the reference material. Target measurement means generates a target output in response to the target detector means in order to determine the amount of fluorescence generated by the target material. Reference calibration means is coupled to the reference measurement means and to the power supply means for varying the electrical voltage supplied to the energy source and for calibrating the reference output. Target calibration means is coupled to the target measurement means for calibrating the target output in response to a known target material. Thus, the apparatus may have the reference measurement means calibrated without a target material, then may have the target measurement means calibrated using the known target material, and then may have the target measurement means determine the fluorescence of the unknown target material.

In a preferred embodiment, the reference detector is a photodiode.

In a preferred embodiment, the apparatus has a first fluorescing wavelength filter optically arranged between the reference material and the photodiode of the reference detector means. The fluorescing first wavelength filter passes light energy at approximately the fluorescing wavelength.

In a preferred embodiment, A second fluorescing wavelength filter is optically arranged between the target material and the photodiode of the target detector means. The second wavelength filter passes light energy at approximately the fluorescing wavelength.

The present invention also provides a method for detecting fluorescence of an unknown target material being excitable at an excitation wavelength and fluorescing at a fluorescing wavelength in an apparatus having a reference material; an energy source arranged to excite both the target material and the reference material at approximately the excitation wavelength; power supply means for supplying electrical power having an adjustable voltage to the energy source; a reference detector means optically arranged to be responsive to the reference material at approximately the fluorescing wavelength; a target detector means optically arranged to be responsive to the target material at approximately the fluorescing wavelength; reference measurement means for generating a reference output in response to the reference detector means in order to determine the amount of fluorescence generated by the reference material; target measurement means for generating a target output in response to the target detector means in order to determine the amount of fluorescence generated by the target material. The method comprises the steps of calibrating the energy source and the reference measurement means without a target material; calibrating the target measurement means using the known target material; and measuring the unknown target material using the target measurement means to determine the fluorescence of the unknown target material.

In a preferred embodiment, the method further comprises the steps of verifying that the energy source is operational; verifying that the reference measurement means is operational; and providing an alarm if the energy source or the reference measurement means is not operational.

In a preferred embodiment, the method further comprises the steps of verifying that the target measurement means is operational; and providing an alarm if the energy source or the target measurement means is not operational.

BRIEF DESCRIPTION OF THE DRAWINGS

The foregoing advantages, construction and operation of the present invention will become more readily apparent from the following description and accompanying drawings in which.

DETAILED DESCRIPTION OF THE PREFERRED EMBODIMENTS

Figure 1:
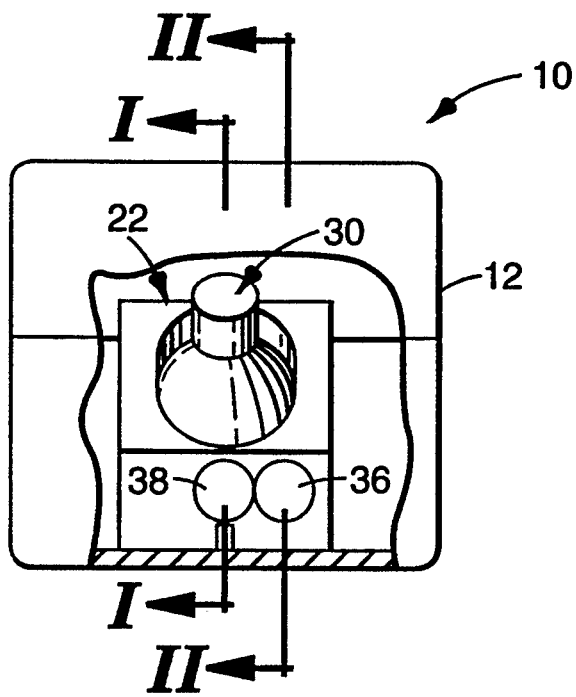
FIG. 1 is an end view of an apparatus constructed in accordance with the present invention.

The preferred apparatus for detecting fluorescence is a fully automated instrument for determining of the relative fluorescence of a sterilization monitor vial. The light source for excitation of the fluorescent material is a halogen lamp held in a stable standby (warm) state, energized to full illumination only when a vial is inserted into a cavity in the instrument housing actuating a light switch. Excitation light from this halogen lamp is guided in two parallel light paths through light filters providing a selected wave length band to the vial and to a fluorescing reference film. Emitted light from the fluorescent film and the from the vial is guided onto separate detectors providing signals for evaluation by a programmed micro-processor. Results of the microprocessor program provide output information of the relative fluorescence and/or the apparatus performance. Normal output information is in the form of yes/no result signal indicated by green or red lights. It is possible to obtain specific values of light output from the vial. Further, the micro-processor provides self-calibration of the system and automatic diagnostics of performance.

Automated operation consists of three phases controlled serially by the micro-processor. Preferably, each phase must be successfully executed before the next can begin, as follows:

First, when the apparatus is energized and before it is operational, a sequence of steps sets the operating condition of the excitation light source and the associated reference signal level. Final sequence step of this phase is to turn on the yellow LED indicating that the apparatus is operational.

Second, following this initial calibration step, a new and unused vial is selected from the current production lot being used for sterilization monitoring and is inserted into the measurement location of the apparatus. The apparatus then calibrates, preferably by a sequence of steps, the vial measurement signal to match the reference signal and, if successful, turns on the green light indicating that the apparatus is in ready status. At this point the new and unused vial is removed and the apparatus remains in a standby status until test vials are ready for analysis. During each of the first two phases a flashing yellow light is turned on if the sequence cannot be completed within predetermined limits.

Third, the apparatus performs actual test (target) vial monitoring. A test (target) vial to be measured is inserted and the green light is turned off. The excitation lamp is energized to full voltage. After, preferably a delay period and, a stabilization period of multiple readings, preferably five, of the light emission of the test vial at the fluorescing wavelength are measured and compared to each other for stability. The lamp voltage is measured and compared with the calibrated value. If the vial measurements fall within a stable range and lamp voltage measurement is within predetermined limits, the apparatus compares the average of the target vial fluorescing wavelength light emissions with the calibrated reference value. If the result is within predetermined limits of the reference value, no active material is present within the vial. The green light, and preferably a beeper, is/are turned on indicating that the test vial is negative. If the result is outside the reference value, preferably plus a threshold value for safety, the red light and a beeper are turned on indicating a positive test indication from the target vial representing the presence of active, unsterilized material in the target vial. If the measurements are not stable, selected warning signals are turned on.

Figure 2:
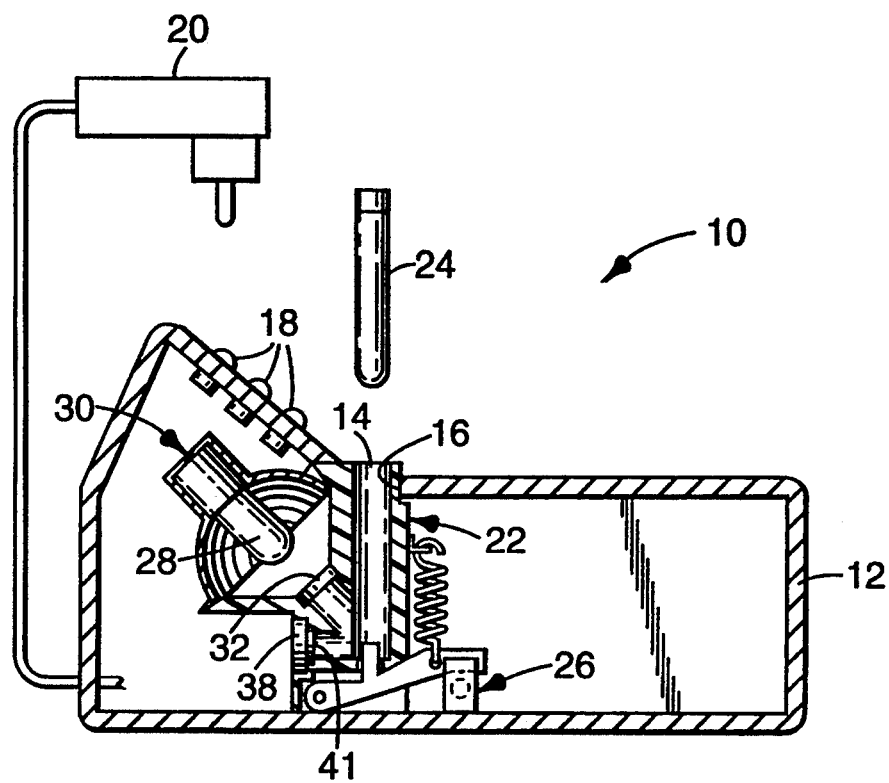
FIG. 2 is a simplified cross-sectional view of the apparatus of FIG. 1 taken along lines I—I.
Figure 3:
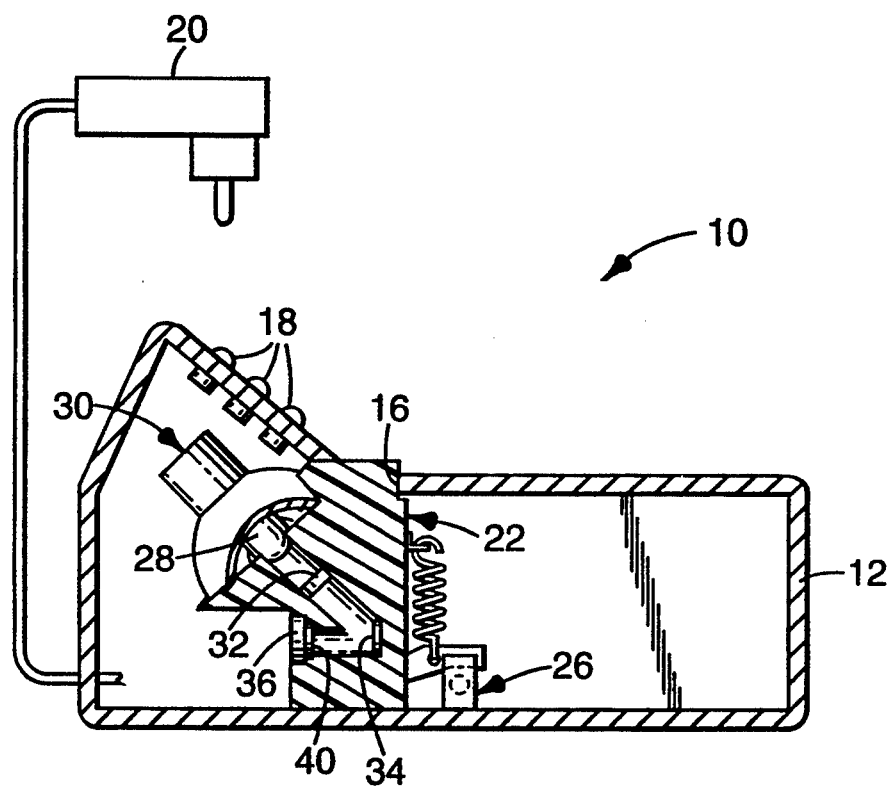
FIG. 3 is a simplified cross-sectional view of the apparatus of FIG. 1 taken along lines II—II.

FIGS. 1, 2 and 3 are drawings illustrating the fluorescence detecting apparatus 10. The housing 12 is roughly three inches (7.62 centimeters) wide, six inches (15.24 centimeters) long and two inches (5.08 centimeters) high. The top surface has an opening 14 allowing entry to a test vial cavity 16, and three lights 18, preferably one each of yellow, red and green. The apparatus 10 is powered by an external power supply 20 providing 15 volts for a 7.5 watt load (0.5 amperes).

Vial cavity assembly 22 is mounted within cavity 16 of housing 12 and is positioned to accept a vial 24. Start sensor 26 is actuated when the vial 24 is inserted into vial cavity assembly 22. Halogen lamp 28, operating as the excitation energy source, is held in socket/reflector assembly 30. Halogen lamp 28 directs excitation wavelength light through ultra-violet band pass excitation filter 32. A fluorescent reference material 34 is positioned parallel to the vial cavity assembly 22 in the excitation light path. A reference sensor 36 and a measurement sensor 38 are positioned parallel to each other in line with vial 24 and reference material 34, respectively. A fluorescing wavelength filter 40, passing wavelengths in the fluorescing range, is positioned between reference material 34 and reference sensor 36 and a similar filter 41 between vial 24 and measurement sensor 38.

Figure 4:
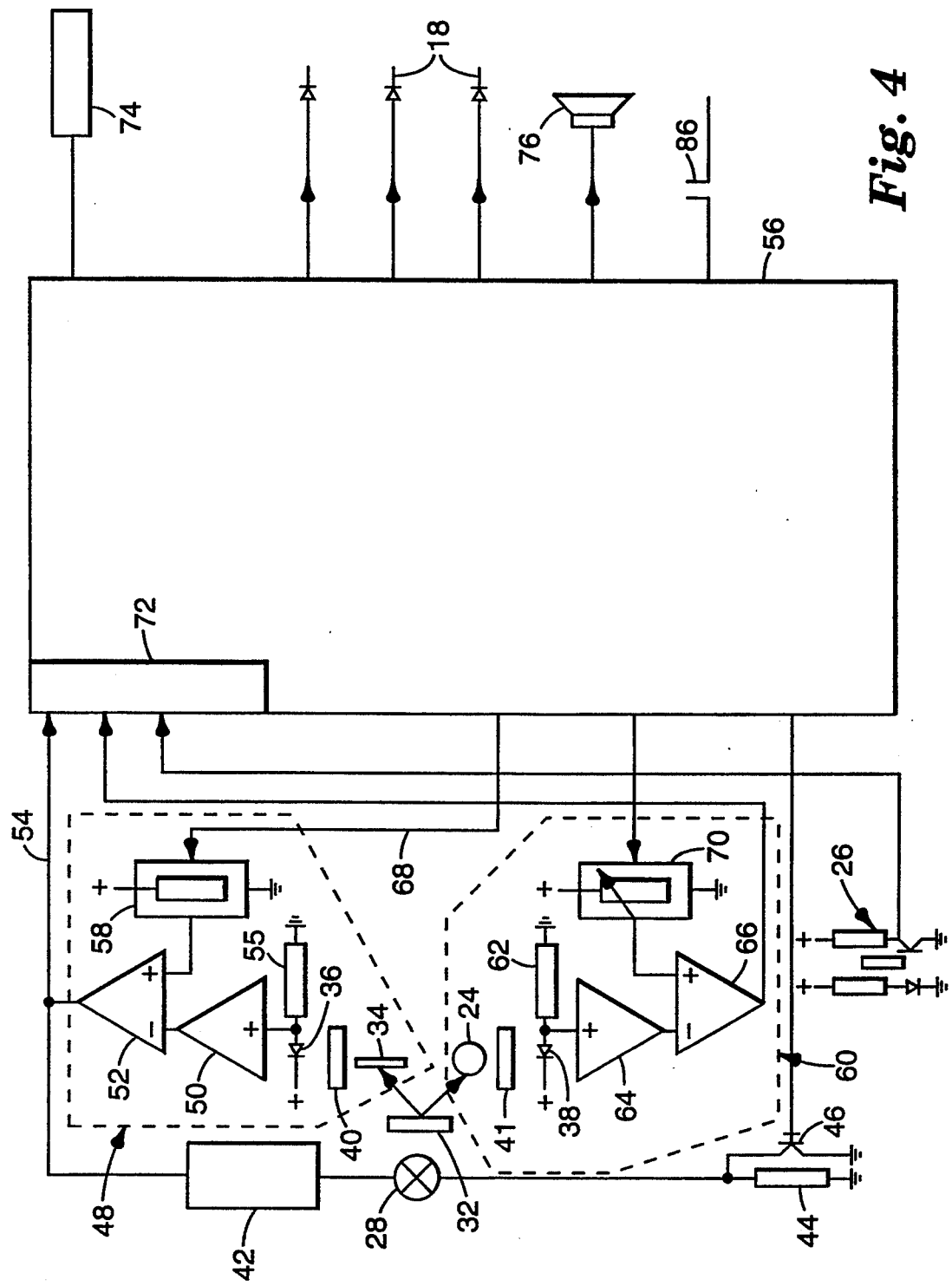
FIG. 4 is a circuit diagram of the apparatus of the present invention.

FIG. 4 is an electrical circuit block diagram of the apparatus 10 for detecting fluorescence. Halogen filled incandescent lamp 28 provides an excitation light source for the apparatus 10. Halogen filled incandescent lamp 28 is a conventional 12 volt 5 watt lamp. Lamp 28 is held in a warm state emitting little or no light at a standby power of approximately 0.33 watts at all times the apparatus 10 is energized from power supply 20. During operation, lamp 28 provides full illumination at above nominal rating, at approximately 118 volts providing above nominal ultraviolet energy for excitation of reference material 34 and test vial 24. The energization voltage to lamp 28 is regulated by voltage control 42. Standby power is limited by resistor 44. Resistor 44 is bypassed by solid state switch 46 during full operating condition. Holding halogen lamp 28 in a warm state allows light output stabilization in less than 1 second following switching to full power. This increases the operating life of lamp 28 by minimizing cold turn-ons and the associated limitation of the high power inrush immediately following turn-on.

Figure 6:
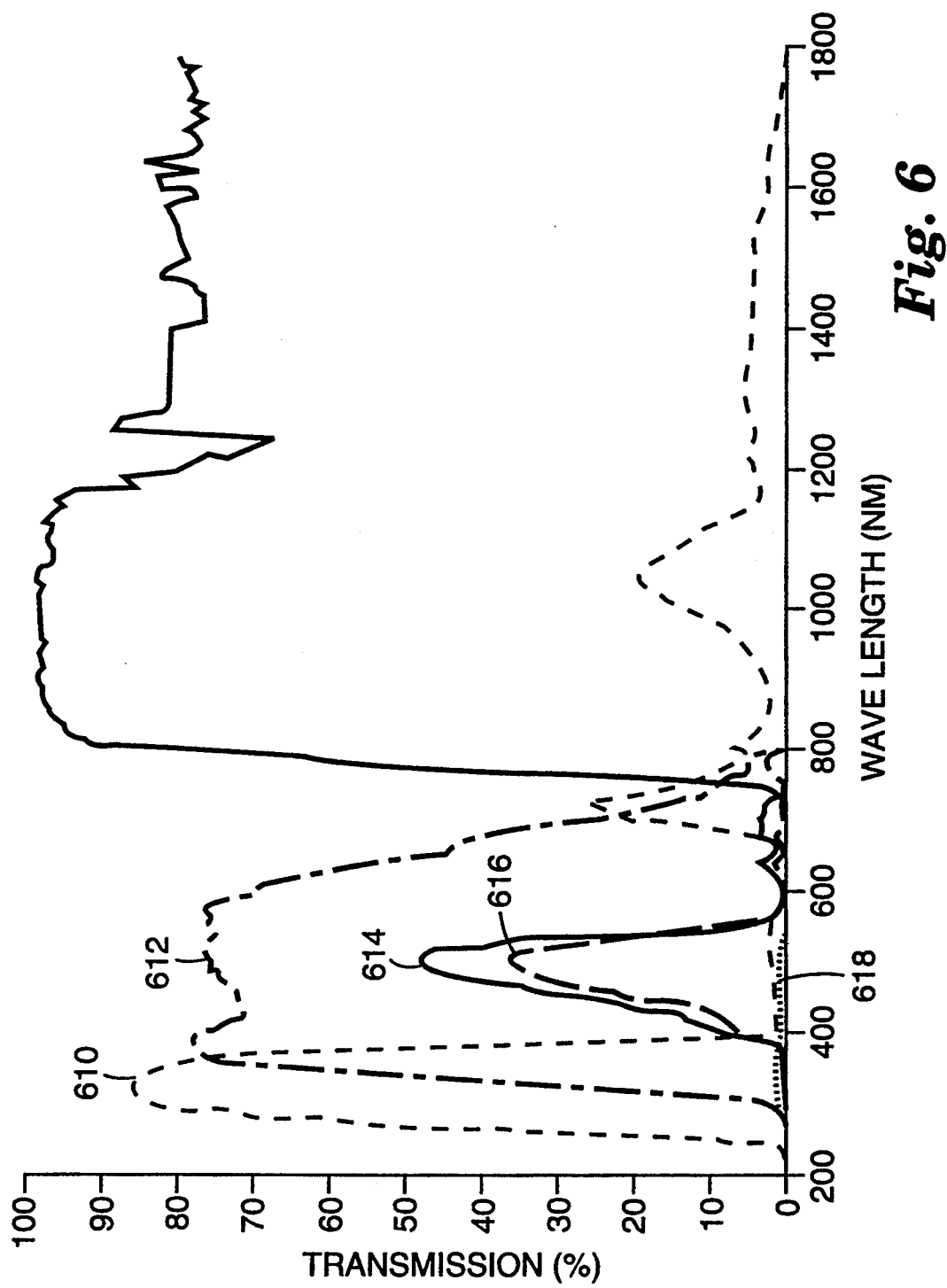
FIG. 6 illustrates the filtering characteristics of the excitation filter of the apparatus of the present invention.

Excitation filter 32 is positioned to pass only excitation wavelength light emitted by lamp 28 as directed in parallel paths to reference material 34 and test vial 24. The excitation wavelength filter is a commonly available 1 millimeter thick UG11 light filter with pass band in the range of 320-380 nanometers, as shown by curve 610 in FIG. 6. Reference emission wavelength light filter 40 is positioned to filter the emitted emission light filter 41 is positioned to filter the emitted light from vial 24 that illuminates measurement sensor 38. Filters 40 and 41 are a combination of a commonly available 2 millimeter thick BG39 light filter as shown by curve 612 and blue colored film as shown by curve 614 providing a combination pass band in the range of 450-550 nanometers as shown by curve 616 in FIG. 6. The combination effect of excitation filter 32 plus the effect of fluorescing filters 40 and 41 is shown by curve 618 of FIG. 6 illustrating that little transmission of light from lamp 28 directly reaches reference sensor 36 or measurement sensor 38.

Apparatus 10 is a dual channel detector which compares the results of two measurements to make a determination of pass or fail. The first measurement is based on the light output from reference material 34 as incident on reference sensor 36. The second measurement is based on light output from the test vial 24 as incident on measurement sensor 38. However, before these measurements and the resultant comparison made, apparatus 10 must be subjected to rigorous calibration to ensure proper operation and accuracy in the results.

Fluorescent reference material 34 includes a fluorescing material that emits light at the nominal wavelength of 450 nanometers when excited by light energy of wavelength within the range of 300 to 400 nanometers. Test vial 24 includes a fluorescent dye that reacts with essentially the same spectra as reference material 34 when test vial 24 is active, i.e., when the sterilization cycle is not effective. The fluorescing material included in reference material 34 is barium magnesium aluminate europium, available from GTE Company, dispersed approximately 2% by dry weight in a clear adhesive coated on a polyethylene substrate and in turn coated with a clear cover to maintain integrity.

Having reference to reference section 48 of FIG. 4, reference material 34 is positioned such that light emitted from reference material 34 passes through fluorescing filter 40 and is incident on reference sensor 36, a photodiode, producing a signal monitored by amplifier 50 and amplifier/comparator 52 producing reference signal 54. Reference sensor 36 is biased by resistor 55. Reference signal 54 is supplied to microprocessor 56 and to voltage control circuit 42. In the preferred reference circuit 48, amplifier 50 has a gain of 6170 and amplifier/comparator 52 has a gain of 33, creating a nominal reference signal 54 voltage of 3.5 volts. Potentiometer 58, under control from microprocessor 56, controls the compare voltage of amplifier/comparator 52.

Having reference to measurement section 60 of FIG. 4, test vial 24 is positioned such that emitted light from any fluorescing material contained in test vial 24 passes through fluorescing filter 41 and is incident on measurement sensor 38, a photodiode, producing a signal whose amplitude is proportional to the amount of light emission from test vial 24. This signal is monitored by amplifier 64 and amplifier/comparator 66 producing a target output signal which is supplied to microprocessor 56 for analysis. In the preferred measurement section 60, amplifier 64 has gain of 3300 and amplifier/comparator 66 has gain of 2. Target output signal 68 is calibrated as discussed below to a voltage of 3.8 volts, thus providing a 0.3 volt margin for a pass or no pass threshold. Measurement sensor 38 is biased by resistor 62. Potentiometer 70, under control from microprocessor 56, controls the compare voltage of amplifier/comparator 66.

Note that the gain of amplifier 50 and amplifier/comparator 52, of reference section 48, is significantly greater than the gain of amplifier 64 and amplifier/comparator 66, of measurement section 60. This makes reference section 48 significantly more sensitive than measurement section 60. The apparatus 10 is balanced after manufacturing. If the manufacturing jumper 86 is connected to microprocessor 56, microprocessor 56 adjusts reference potentiometer 58 to mid-range. A mechanical shutter (not shown) is then employed between reference material 34 and reference sensor 36 to adjust reference signal 54 to a predetermined operational set point, preferably 3.5 volts. Microprocessor 56 controls the operator by red light (turn screw right) or green light (turn screw left) or flashing green and red lights (finished).

Microprocessor 56 receives digital information inputs through analog-to-digital convertor 72 from reference signal 54 and measurement signal 68 as well as a signal from start sensor 26. Microprocessor program memory is contained in conventional memory 74. Microprocessor 56 follows a program as diagrammed in FIG. 5 and discussed below. Microprocessor controls digital potentiometer 58 and digital potentiometer 70 and supplies appropriate information to lights 18 and auditory warning device 76, a buzzer, during calibration and operation also as discussed below.

Figure 5:
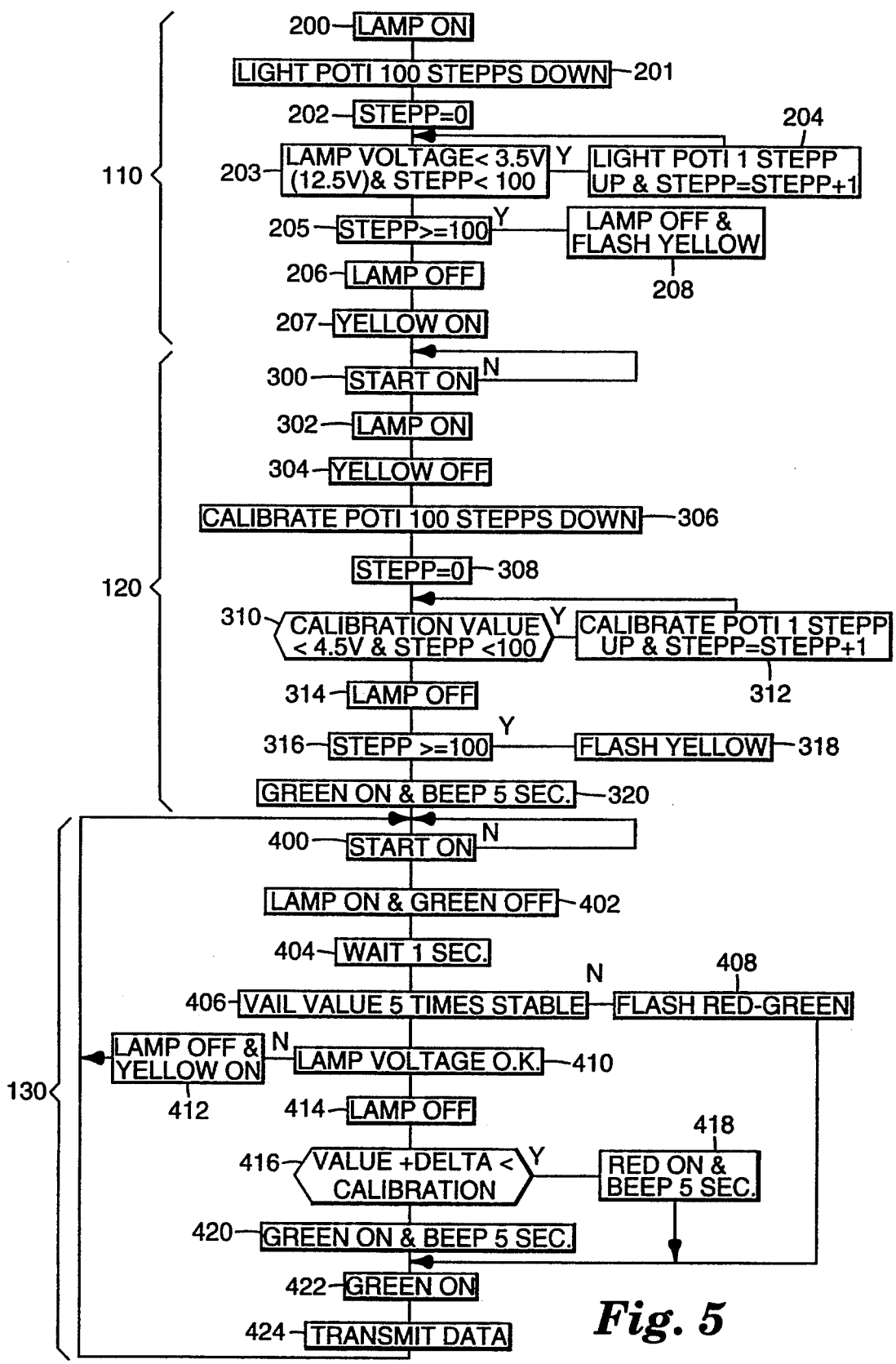
FIG. 5 is a flow diagram illustrating the sequencing of operations controlled by the microprocessor of the apparatus of the present invention.

Calibration of lamp 28 is first accomplished in reference section 48 under control of microprocessor 56 as illustrated portion 110 of FIG. 5. When the apparatus 10 is energized, e.g., by plugging in power supply 20, at the beginning of a work period, lamp 28 is energized (step 200). Digital potentiometer 58 is set to zero (step 201) which drives the voltage to lamp 28 below predetermined operating point. A step counter is set to zero (step 202). However, light continues to impinge reference sensor 36 resulting in stable feedback at a low value of reference voltage 54. Successive iterations (steps 203 and 204) increase digital potentiometer 58 and increases the voltage at lamp 28 and the associated light emission until reference signal 54 reaches a predetermined level, e.g. 2.8 volts. At this point, lamp 28 is turned off (step 206) and the yellow light 18, a light emitting diode, is turned on (step 207) indicating that the apparatus 10 as operational.

Reference section 48 provides a negative feedback loop so that if lamp 28 is not operational, no light impinges upon reference sensor 36 or if any of the component parts of reference section 48 malfunction, the feedback loop is interrupted and the iterative sequence continues moving potentiometer 58 to step number 100 where lamp 28 is turned off (step 208) and yellow light 18 flashes. No further steps are allowed in the sequence of operation.

Provided that the steps outlined in portion 110 of FIG. 5 are accomplished successfully, automated calibration of the apparatus 10 proceeds as illustrated in portion 120 of FIG. 5. Calibration of the apparatus 10 is required each time it is energized and each time a new lot of test (target) vials is used. Any new and unused test vial will have a minor background level of fluorescent light emission due to the materials and processing used in manufacture, the level of emission is stable in time but varies from lot to lot, thus for the comparative test this background emission must be calibrated out for evaluating active vials. A new and unused vial 24, from the selected manufacturing lot, into vial cavity assembly 22 and pressed down to actuate start sensor 26 (step 300). Lamp 28 is turned on (step 302), yellow light 18 is turned off (step 304), and digital potentiometer 70 is set to zero (steps 306 and 308) driving the value of measurement signal 68 to a low level, e.g., below 0.5 volts. Successive iterations (steps 310 and 312) move digital potentiometer 70 until the voltage of measurement signal 68 reaches a predetermined level. Lamp 28 is then turned off (step 314) and a green light 18 is turned on and a beeping sound is emitted from buzzer 76 indicating that apparatus 10 is ready for use (step 320). In the preferred circuit arrangement, the predetermined value for measurement signal 68 is 3.8 volts.

If any of the circuit components malfunction or if the test vial emits no light, the successive iterations of digital potentiometer 70 will continue until a predetermined maximum of 100 steps is reached (step 316). Step 316 then causes The yellow light 18 is set to flash (step 318) and further steps in the sequence are blocked.

The apparatus 10 is then ready for the operating sequence for testing the target sterilization monitoring vials as illustrated in portion 130 of FIG. 5. After the apparatus 10 is calibrated as described above, a target vial is inserted as a test vial 24 into vial cavity assembly 22 and pressed down to activate start sensor 26 (step 400). Lamp 28 is energized to full illumination and a green light 18, which indicates ready status, is turned off (step 402). After a one second delay (step 404) to stabilize light output of the halogen lamp 28, a series of five separate readings of the target output signal are recorded over a period of less than one second (step 406). If these values, when compared to each other, have less than a predetermined variance tolerance, preferably 0.1 volts, the lamp 28 voltage is checked (step 410), and lamp 28 is turned off (Step 414). Target vial measurement continues by comparing an average of the five readings plus a error threshold with the calibration voltage (step 416), as the output was inverted. If the result is greater than the calibration voltage, the green light 18 is turned on and buzzer 76 is sounded (step 420) for five seconds indicating a negative target vial, i.e., the target vial passes the sterilization test. However, if the result is less than the calibration voltage, the red light 18 is turned on and buzzer 76 is sounded for five seconds (step 418) indicating a positive vial and failure of the sterilization test. If the five vial measurements (step 406) are not stable, a warning is indicated with flashing red and green lights 18 (step 408) and the operating sequence is halted. In either case apparatus 10, blocks further steps in the sequence until vial 24 is removed. After removal of vial 24, the green light 18 is turned on and the apparatus 10 returned to ready status (step 422).

If the voltage of lamp 28 is not in range (step 410), preferably the reference voltage of 3.5 volts, yellow light 18 is turned on (step 412) and the operating sequence is interrupted.

Figure 7A:
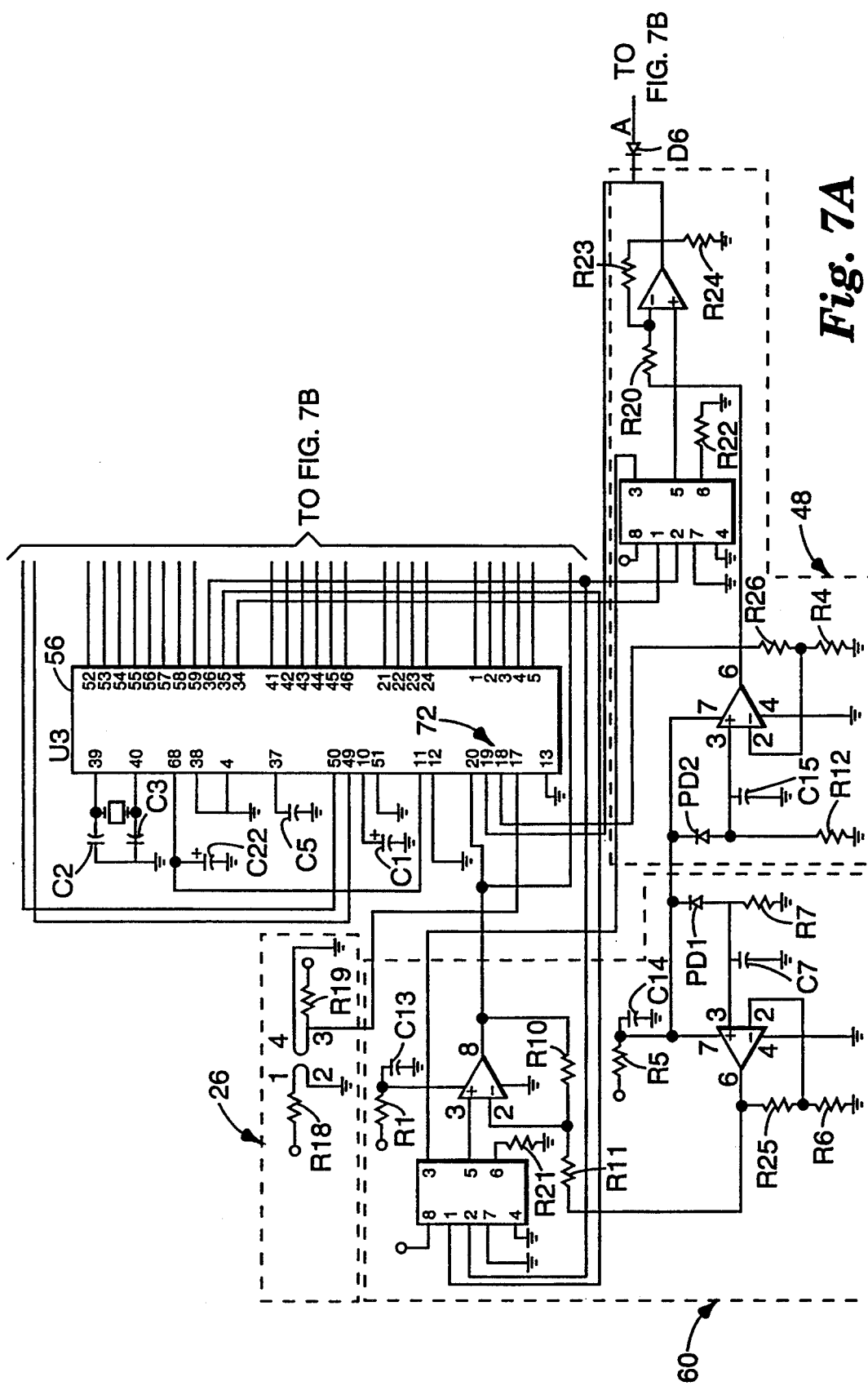
FIGS. 7a and 7b are a detailed circuit diagram of a preferred embodiment of the apparatus of the present invention.
Figure 7B:
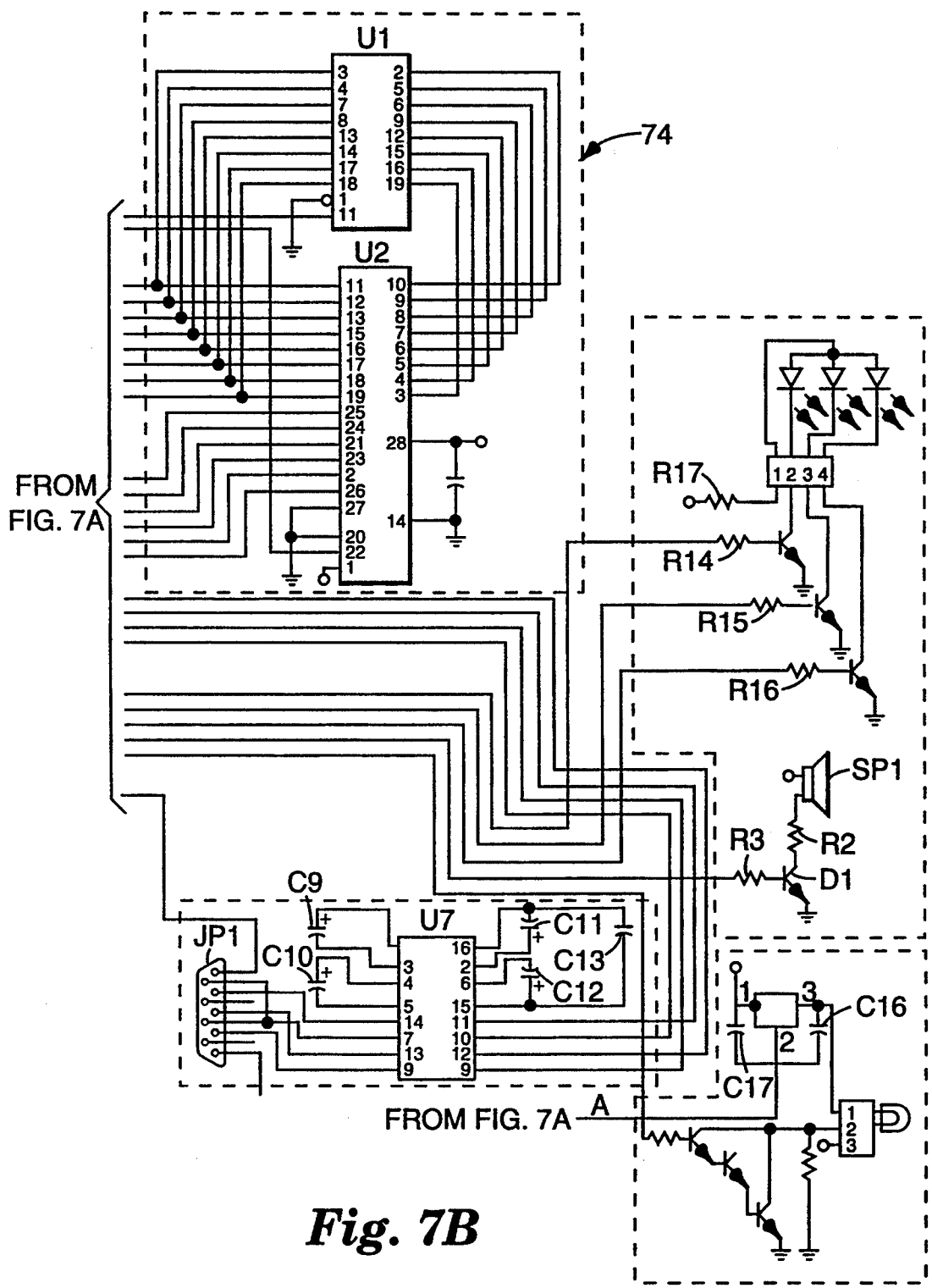
Figure 7A:
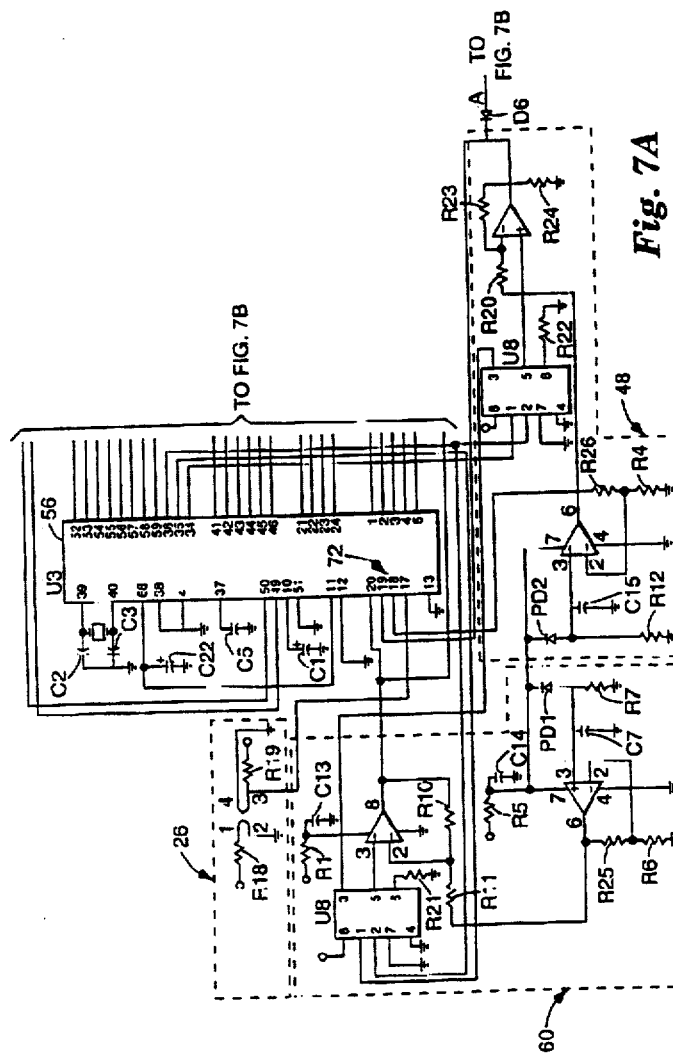
Figure 5:
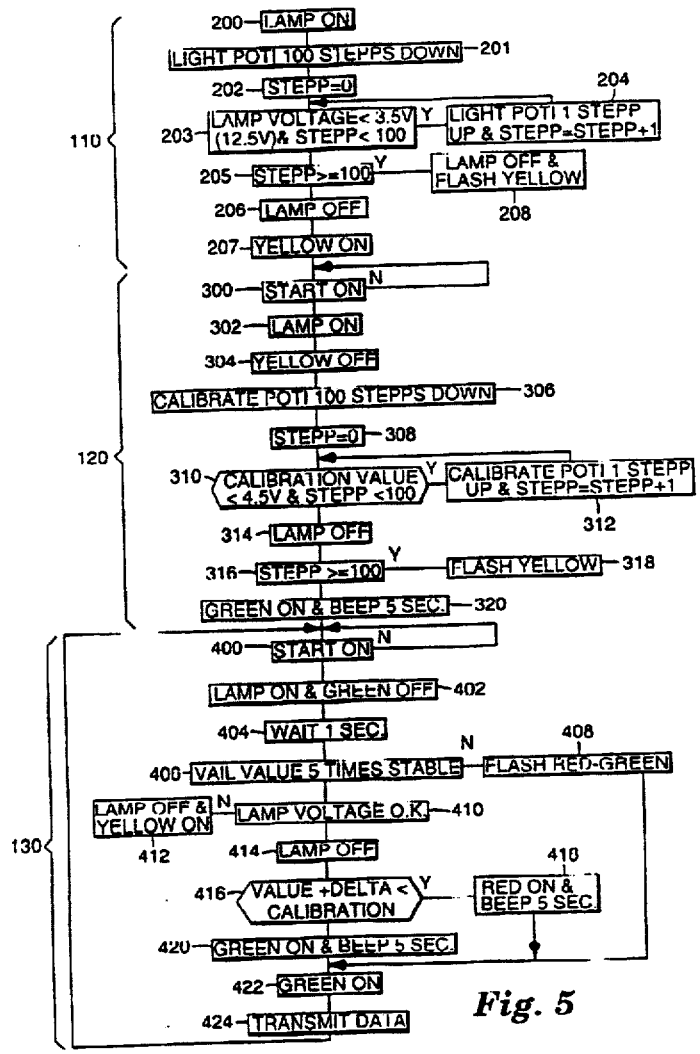

A detailed circuit diagram is illustrated in FIGS. 7a and 7b whose component values and component identifications are contained in the following Table:

TABLE I

| Reference Numeral | Component | Value or Identification |
|---|---|---|
| U1 | 74HCT373 | Eight Bit Latch |
| U2 | 27C256 | 32K*8 EPROM |
| U3 | SAB 80C535 | 8-bit Microcontroller |
| U4 | 7805CKC | 5 volt/1 ampere Voltage Regulator |
| U5 | X9103 | Digitally Controlled Potentiometer |
| U6 | TLC2201A | Operational Amplifier |
| U7 | MAX232 | Dual RS-232 Transmitter/Receiver |
| U8 | X9103 | Digitally Controlled Potentiometer |
| U9 | TLC2201A | Operational Amplifier |
| U10 | TLC272B | Dual Operational Amplifier |
| U11 | 7809CKC | 9 volt/1 ampere Voltage Regulator |
| D1 | TLLR 5401 | LED LP Red |
| D2 | TLLG 5401 | LED LP Green |
| D3 | TLLY 5401 | LED LP Yellow |
| D4 | ZY 6.8 | Zener Diode, 1 watt |
| D6 | 1N4148 | Diode, 0.5 watt |
| D7 | TCST1301 | Light Switch |
| PD1 | BPW21 | Photodiode |
| PD2 | DPW21 | Photodiode |
| R1 | 100 ohms | Resistor, 0.6 watt |
| R2 | 330 ohms | Resistor, 0.6 watt |
| R3 | 10 kilohms | Resistor, 0.6 watt |
| R4 | 100 ohms | Resistor, 0.6 watt |
| R5 | 100 ohms | Resistor, 0.6 watt |
| R6 | 100 ohms | Resistor, 0.6 watt |
| R7 | 1 megohm | Resistor, 0.6 watt |
| R8 | 10 kilohms | Resistor, 0.6 watt |
| R9 | 470 ohms | Resistor, 0.6 watt |
| R10 | 11 kilohms | Resistor, 0.6 watt |
| R11 | 11 kilohms | Resistor, 0.6 watt |
| R12 | 1 megohm | Resistor, 0.6 watt |
| R14 | 10 kilohms | Resistor, 0.6 watt |
| R15 | 10 kilohms | Resistor, 0.6 watt |
| R16 | 10 kilohms | Resistor, 0.6 watt |
| R17 | 3.3 kilohms | Resistor, 0.6 watt |
| R18 | 680 ohms | Resistor, 0.6 watt |
| R19 | 10 kilohms | Resistor, 0.6 watt |
| R20 | 1 kilohm | Resistor, 0.6 watt |
| R21 | 100 ohms | Resistor, 0.6 watt |
| R22 | 100 ohms | Resistor, 0.6 watt |
| R23 | 33 kilohms | Resistor, 0.6 watt |
| R24 | 1 kilohms | Resistor, 0.6 watt |
| R25 | 330 kilohms | Resistor, 0.6 watt |
| R26 | 617 kilohms | Resistor, 0.6 watt |
| P1 | 10 kilohm | Potentiometer Preh 8, 6 |
| C1 | 1 microfarad, 35 volt TANT | Capacitor |
| C2 | 33 picofarad, 50 volt KER | Capacitor |
| C3 | 33 picofarad, 50 volt KER | Capacitor |
| C4 | 0.1 microfarad, 35 volt TANT | Capacitor |
| C5 | 68 nanofarad, 63 volt KUNST | Capacitor |
| C6 | 0.22 microfarad, 35 volt TANT | Capacitor |
| C7 | 100 nanofarad, 63 volt KUNST | Capacitor |
| C8 | 100 nanofarad, 63 volt KUNST | Capacitor |
| C9 | 10 microfarad, 16 volt TANT | Capacitor |
| C10 | 10 microfarad, 16 volt TANT | Capacitor |
| C11 | 10 microfarad, 16 volt TANT | Capacitor |
| C12 | 10 microfarad, 16 volt TANT | Capacitor |
| C13 | 10 microfarad, 16 volt TANT | Capacitor |

TABLE I-continued

| Reference Numeral | Component | Value or Identification |
| --- | --- | --- |
| C14 | 100 nanofarad, 63 volt KUNST | Capacitor |
| C15 | 100 nanofarad, 63 volt KUNST | Capacitor |
| C16 | 0.1 microfarad, 35 volt TANT | Capacitor |
| C17 | 0.22 microfarad, 35 volt TANT | Capacitor |
| C18 | 1,000 microfarad, 16 volt ELCO | Capacitor |
| C19 | 1 nanofarad, 200 volt CK05 | Capacitor |
| C20 | 1 nanofarad, 200 volt CK05 | Capacitor |
| C21 | 100 nanofarad, 63 volt KUNST | Capacitor |
| C22 | 10 microfarad, 16 volt TANT | Capacitor |
| JP1 | 9 pole male SUB-D | Connector |
| JP2 | 3P AMP MODU 2 | Connector |
| JP3 | 2.1 ROKA | Connector |
| JP4 | 5P AMP MODU 2 | Connector |
| L1 | 12 volt, 5 watt 64111 Halogen OSRAM | Lamp |
| X1 | HC-18U | 12 MegaHertz Quartz |
| DR1 | 2943666671 | FAIR-RITE Shield Beads |
| SP1 | HMB-12 | DIGISOUND Beeper |
| Q1 | BC548C | NPN Transistor |
| Q2 | BC517 | Darlington NPN Transistor |
| Q3 | BC548C | NPN Transistor |
| Q4 | BC548C | NPN Transistor |
| Q5 | BC548C | NPN Transistor |
| Q6 | BC368 | NPN Transistor |

Thus, it can be seen that there has been shown and described a novel invention as described above. It is to be recognized and understood, however, that various changes, modifications and substitutions in the form and the details of the present invention may be made by those skilled in the art without departing from the scope of the invention as defined by the following claims.

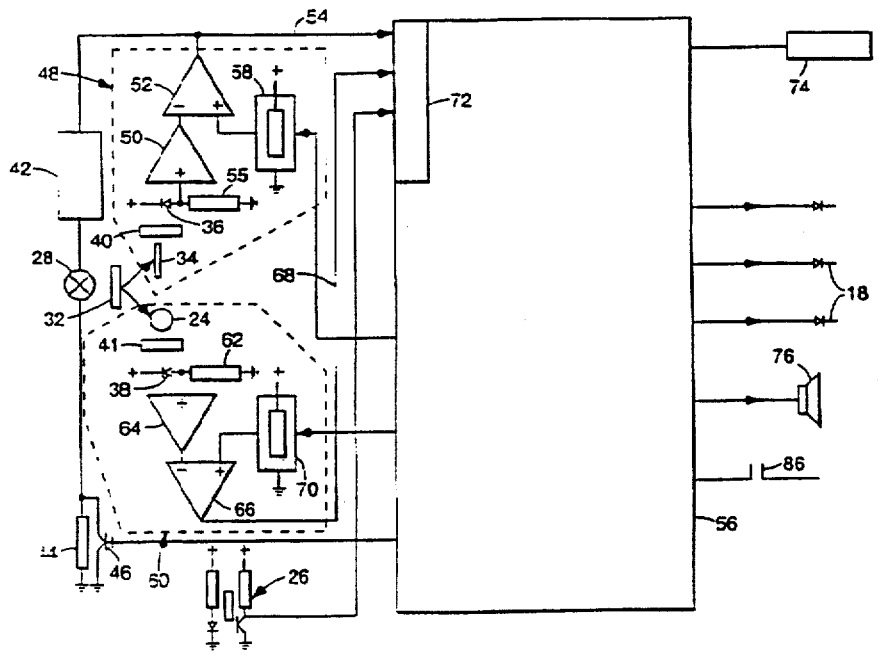

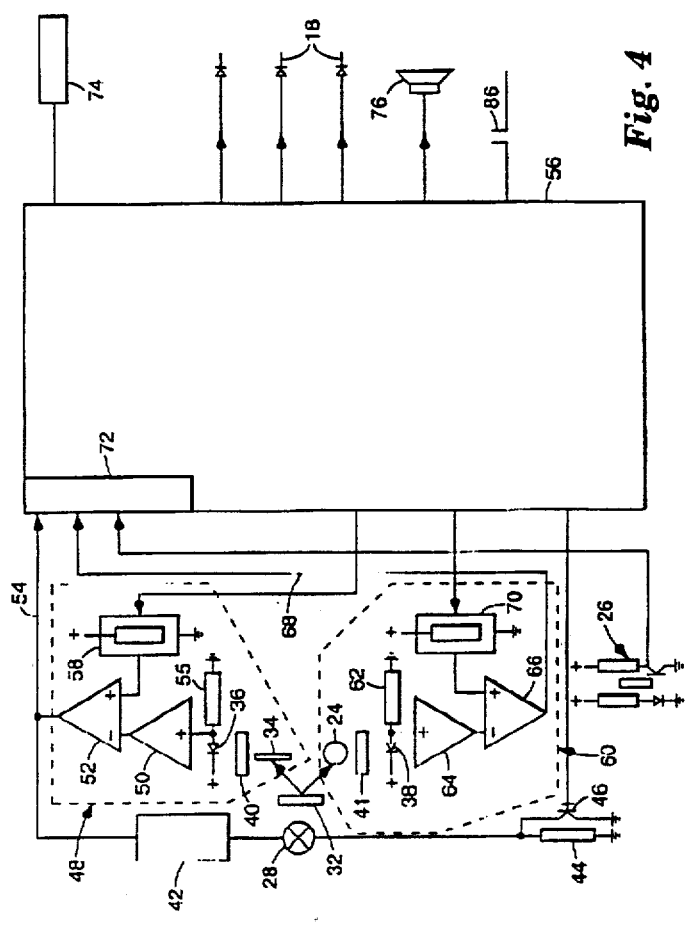

What is claimed is:

1. An apparatus for detecting fluorescence of an unknown target material being excitable at an excitation wavelength and fluorescing at a fluorescing wavelength, comprising:

a reference material;

an energy source arranged to excite both said target material and said reference material at approximately said excitation wavelength;

power supply means for supplying electrical power having an adjustable voltage to said energy source;

an excitation filter optically arranged between said energy source and both of said target material and said reference material, said excitation filter passing light energy at approximately said excitation wavelength;

a reference detector means optically arranged to be responsive to and for detecting light emitted from said reference material at approximately said fluorescing wavelength;

a target detector means optically arranged to be responsive to and for detecting light emitted from said target material at approximately said fluorescing wavelength;

reference measurement means for generating a reference output in response to said reference detector means in order to determine the amount of fluorescence generated by said reference material;

target measurement means for generating a target output in response to said target detector means in order to determine the amount of fluorescence generated by said target material;

reference calibration means coupled to said reference measurement means and to said power supply means for varying the electrical voltage supplied to said energy source and for calibrating said reference output; and target calibration means coupled to said target measurement means for calibrating said target output in response to a known target material.

2. An apparatus for detecting fluorescence as in claim 1 wherein said reference detector means comprises a photodiode.

3. An apparatus for detecting fluorescence as in claim 2 further comprising a first fluorescing wavelength filter optically arranged between said reference material and said photodiode of said reference detector means, said fluorescing first wavelength filter passing light energy at approximately said fluorescing wavelength.

4. An apparatus for detecting fluorescence as in claim 3 which further comprises a second fluorescing wavelength filter optically arranged between said target material and said photodiode of said target detector means, said second wavelength filter passing light energy at approximately said fluorescing wavelength.

5. An apparatus for detecting fluorescence as in claim 4 in which said reference material comprises a fluorescing material that emits light at the nominal wavelength of 450 nanometers when excited by light energy of wavelength within the range of 300 to 400 nanometers consisting essentially of barium magnesium aluminate europium dispersed approximately 2% by dry weight in a clear adhesive coated on a polyethylene substrate and in turn coated with a clear cover to maintain integrity.

6. A method for detecting fluorescence of an unknown target material being excitable at an excitation wavelength and fluorescing at a fluorescing wavelength in an apparatus having a reference material; an energy source arranged to excite both said target material and said reference material at approximately said excitation wavelength; power supply means for supplying electrical power having an adjustable voltage to said energy source; a reference detector means optically arranged to be responsive to said reference material at approximately said fluorescing wavelength; a target detector means optically arranged to be responsive to said target material at approximately said fluorescing wavelength; reference measurement means for generating a reference output in response to said reference detector means in order to determine the amount of fluorescence generated by said reference material; target measurement means for generating a target output in response to said target detector means in order to determine the amount of fluorescence generated by said target material, comprising the steps of:

calibrating said energy source and said reference measurement means without a target material;

calibrating said target measurement means using a known target material; and measuring said unknown target material using said target measurement means to determine said fluorescence of said unknown target material.

7. A method for detecting fluorescence as in claim 6 which further comprises the steps of:

verifying that said energy source is operational;

verifying that said reference measurement means is operational; and providing an alarm if said energy source or said reference measurement means is not operational.

8. A method for detecting fluorescence as in claim 6 which further comprises the steps of:

verifying that said target measurement means is operational; and providing an alarm if said energy source or said target measurement means is not operational.

* * * * *

UNITED STATES PATENT AND TRADEMARK OFFICE
CERTIFICATE OF CORRECTION

PATENT NO : 5,334,841

DATED : August 2, 1994

INVENTOR(S) : Josef A. Graessle, et. al.

It is certified that error appears in the above-identified patent and that said Letters Patent is hereby corrected as shown below:

The title page, showing an illustrative figure 4 should be deleted and substituted therefor figure 4 on the attached title page.

Figures 5 and 7A, should be deleted to be replaced with figures 5 and 7A shown on the attached sheet.

Signed and Sealed this

Third Day of January, 1995

*Attest:*

BRUCE LEHMAN

*Attesting Officer*     Commissioner of Patents and Trademarks

United States Patent [19]

Graessle et al.

[11] Patent Number: 5,334,841

[45] Date of Patent: Aug. 2, 1994

[54] METHOD AND APPARATUS FOR DETECTING FLUORESCENCE

[75] Inventors: Josef A. Graessle, Kaarst; Werner R. Schwarz, Leverkusen, both of Fed. Rep. of Germany; William E. Foltz, Cottage Grove, Minn.

[73] Assignee: Minnesota Mining and Manufacturing Company, St. Paul, Minn.

[21] Appl. No.: 7,758

[22] Filed: Jan. 22, 1993

[51] Int. Cl.$^5$ .............................................. G01N 21/64
[52] U.S. Cl. .............................. 250/458.1; 250/459.1; 250/461.1
[58] Field of Search ............... 250/252.1 A, 458.1, 250/461.1, 459.1, 461.2; 356/317

[56] References Cited

U.S. PATENT DOCUMENTS

| | | | |
|---|---|---|---|
| 4,622,468 | 11/1986 | Stefanski et al. | 250/458.1 |
| 4,626,684 | 12/1986 | Landa | 250/328 |
| 4,668,868 | 5/1987 | Noller | 250/458 |
| 5,030,297 | 7/1991 | Vespermann et al. | 148/12 F |
| 5,030,832 | 7/1991 | Williams et al. | 250/458.1 |
| 5,032,730 | 7/1991 | Iwasaki | 250/461.2 |
| 5,063,297 | 11/1991 | Hardenbrook et al. | 250/458.1 |
| 5,073,488 | 12/1991 | Matner et al. | 435/31 |

Primary Examiner—Carolyn E. Fields
Attorney, Agent, or Firm—Gary L. Griswold; Walter N. Kirn; William D. Bauer

[57] ABSTRACT

An apparatus and method for detecting fluorescence of an unknown target material. An energy source arranged to excite both the target material and the reference material at approximately the excitation wavelength. A reference detector and a target detector are optically arranged to be responsive to light emitted from the reference material and the target material, respectively, at approximately the fluorescing wavelength. A reference measurement means generates a reference output in response to the reference detector in order to determine the amount of fluorescence generated by the reference material. A target measurement means generates a target output in response to the target detector means in order to determine the amount of fluorescence generated by the target material. Reference calibration means varies the electrical voltage supplied to the energy source and calibrates the reference output. Target calibration means calibrates the target output in response to a known target material.

8 Claims, 7 Drawing Sheets